United States Patent [19]

Glass

[11] Patent Number: 5,564,681
[45] Date of Patent: Oct. 15, 1996

[54] WORK STATION FOR USE IN CONJUNCTION WITH A VISE

[76] Inventor: Carey Glass, 21 S. First Ave., Highland Park, N.J. 08904

[21] Appl. No.: 408,054
[22] Filed: Mar. 21, 1995
[51] Int. Cl.⁶ ........................................... B25B 1/24
[52] U.S. Cl. ...................... 269/271; 269/282; 269/289 R
[58] Field of Search .......................... 269/99, 100, 155, 269/282, 271, 277, 282, 289 R; 144/287, 286 A

[56] References Cited

U.S. PATENT DOCUMENTS

| | | |
|---|---|---|
| 2,499,408 | 3/1950 | Nipken . |
| 2,779,219 | 1/1957 | Lassy . |
| 2,908,303 | 10/1959 | Schmidt .................................. 269/100 |
| 4,054,068 | 10/1977 | Carter . |
| 4,266,420 | 5/1981 | Walker .................................... 269/277 |
| 4,413,818 | 11/1983 | Lenz . |
| 4,534,546 | 8/1985 | Cattani . |
| 4,750,722 | 6/1988 | Chick ...................................... 269/155 |
| 4,805,888 | 2/1989 | Bishop ...................................... 269/99 |
| 4,911,419 | 3/1990 | Deakin et al. ........................... 269/277 |
| 4,927,126 | 5/1990 | Hoffman . |
| 4,969,637 | 11/1990 | Nishimura . |

Primary Examiner—Robert C. Watson
Attorney, Agent, or Firm—Watov & Kipnes

[57] ABSTRACT

Apparatus for use in conjunction with a vise to provide a secured work station in which the vise grips the vise engaging device connected to the work station with a first locking force in a first direction and a locking assembly is provided to secure the vise engaging device with a second locking force in a second direction different than the first direction.

6 Claims, 3 Drawing Sheets

WORK STATION FOR USE IN CONJUNCTION WITH A VISE

FIELD OF THE INVENTION

The present invention is directed to a work station for use in conjunction with a dual-jawed vise in which the work station is maintained firmly within the vise by a locking assembly in the form of a T-shaped bar.

BACKGROUND OF THE INVENTION

Work stations used in conjunction with a vise are employed in a number of industries including the manufacture of prosthetic and/or orthotic devices. One such work station can be in the form of or associated with an elongated bar. A vise typically having a pair of opposed jaws can be used to lock the work station therebetween. The jaws of the vise are moved into locking engagement with side surfaces of the work station and if sufficient force is applied to the jaws in a single direction, the work station will remain secured.

However, there are work operations, such as hammering and the like, which place a significant force against the work station. If the force against the work station resulting from the work operation exceeds the locking force applied by the jaws against the work station in a single direction, then the work station can become dislodged from the vise.

If the work station becomes dislodged, the jaws must be loosened and the locking operation performed again using an even greater locking force. Thus, the dislodging of the work station results in the loss of production time.

There is another detriment that arises with conventional assemblies of vise associated work stations. The force applied to the work station, if sufficient to dislodge the same, can also cause damage to the jaws including the stripping of the threads used to apply the torque necessary to provide a locking force to the jaws.

A conventional solution to the problem is to apply an even greater unidirectional locking force to the work station. However, this approach to the problem is only short-lived and can eventually result in even more significant damage to the vise.

It would therefore be a significant advance in the art of work stations used in conjunction with a vise to provide an arrangement for locking the work station in a manner in which multiple locking forces in multiple directions are applied to the work station. As a result, the work station cannot easily become dislodged under severe work operations such as hammering and the like.

SUMMARY OF THE INVENTION

The present invention is directed to a work station for use in conjunction with a vise in which the work station is securely locked into place by an assembly that interlocks the work station and the vise together without relying solely upon the force applied by the vise itself to the work station.

More specifically, the present invention is directed to a work station for use in conjunction with a vise having opposed jaws comprising:

a) a work station having an upper side and a lower side, said upper side including a work surface and a lower side comprising a vise engaging means;

b) a vise engaging means operatively connected to the work station having opposed sides for engagement by the opposed jaws of the vise to provide a first locking force in a first direction; and c) a locking assembly for securing the vise engaging means and the vise in operative locking engagement, said locking assembly comprising a T-shaped bar having respective surfaces for engaging the opposed jaws of the vise and connecting means for connecting the locking assembly to the vise engaging means, said locking assembly applying a second locking force in a second direction different than the first direction.

The locking assembly of the present invention provides multiple locking forces in different directions to provide a work station which is secured within the vise.

BRIEF DESCRIPTION OF THE DRAWINGS

The following drawings in which like reference characters indicate like parts are illustrative of embodiments of the invention and are not intended to limit the invention as encompassed by the claims forming part of the application.

DETAILED DESCRIPTION OF THE INVENTION

The present invention is directed to a work station for use in conjunction with a vise in which a locking assembly secures the work station to the vise. Accordingly, the work station cannot be dislodged even when a significant force (e.g. by hammering and the like) is applied to the work station. The present invention also prevents damage to the vise even under severe loads.

Figure 1:
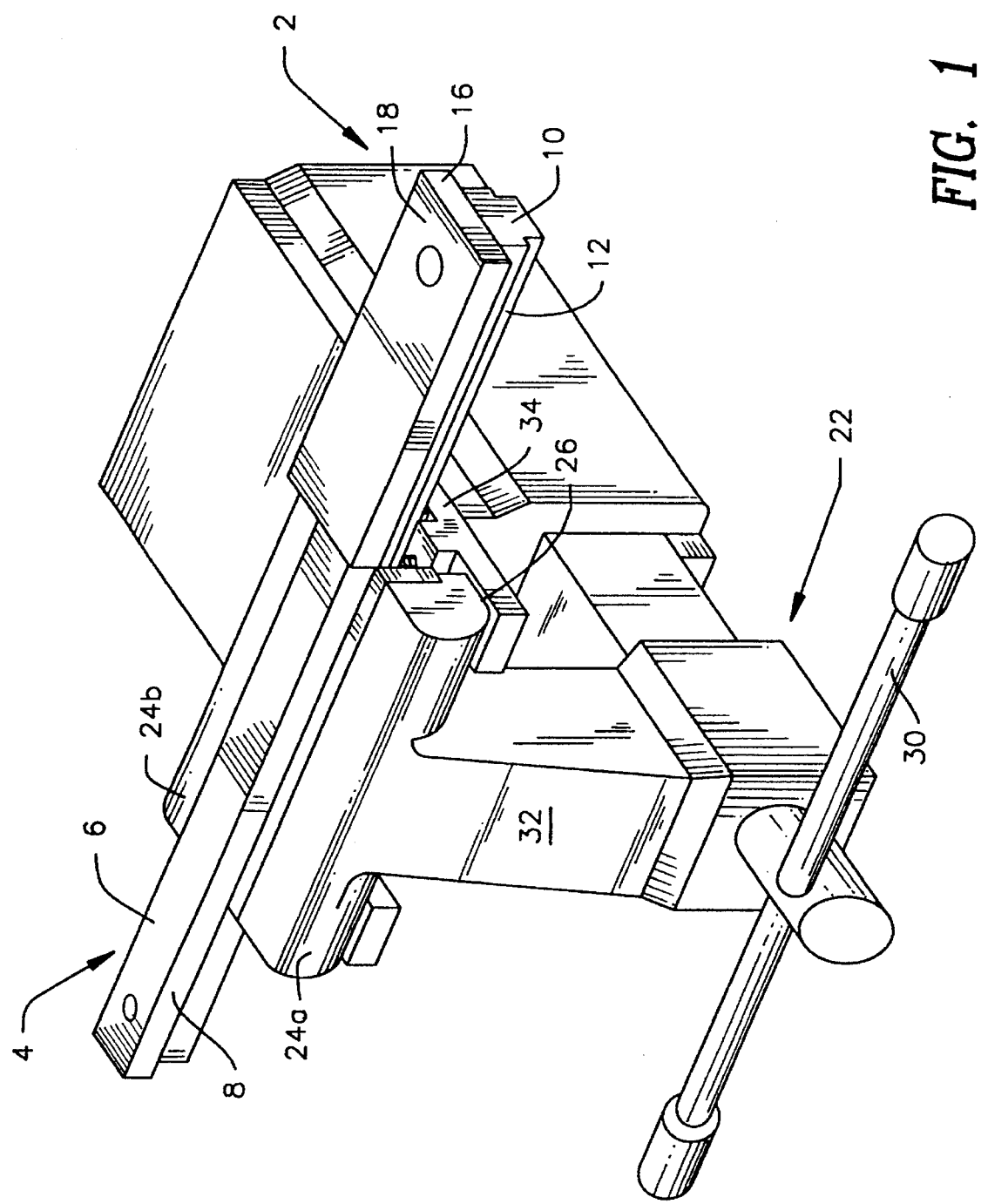
FIG. 1 is a perspective view of the work station of the present invention secured in a vise.

Referring to the drawings and first to FIG. 1, there is shown a work station of the present invention secured to a vise. Specifically, a work station 2 includes an elongated bar 4 having an upper surface 6, opposed side surfaces 8, a downwardly extending projection 10 having opposed side surfaces 12 and a bottom surface 14 (see FIG. 3).

The upper surface 6 of the bar 4 may be employed as a working surface or, as shown specifically in FIG. 1, a platform 16 having a working surface 18 may be used. The platform 16 is operatively attached to the bar 4 through a screw (not shown) inserted through a hole 20 in the platform 16 and a corresponding hole 22 (shown only on the opposite end of the bar) in the bar 4.

The platform 16 provides a flat working surface 18 which may be used to work on flat objects or hollow objects such as prosthetic devices. The type of working operations that may be performed on the work station 2 are unlimited.

Figure 3:
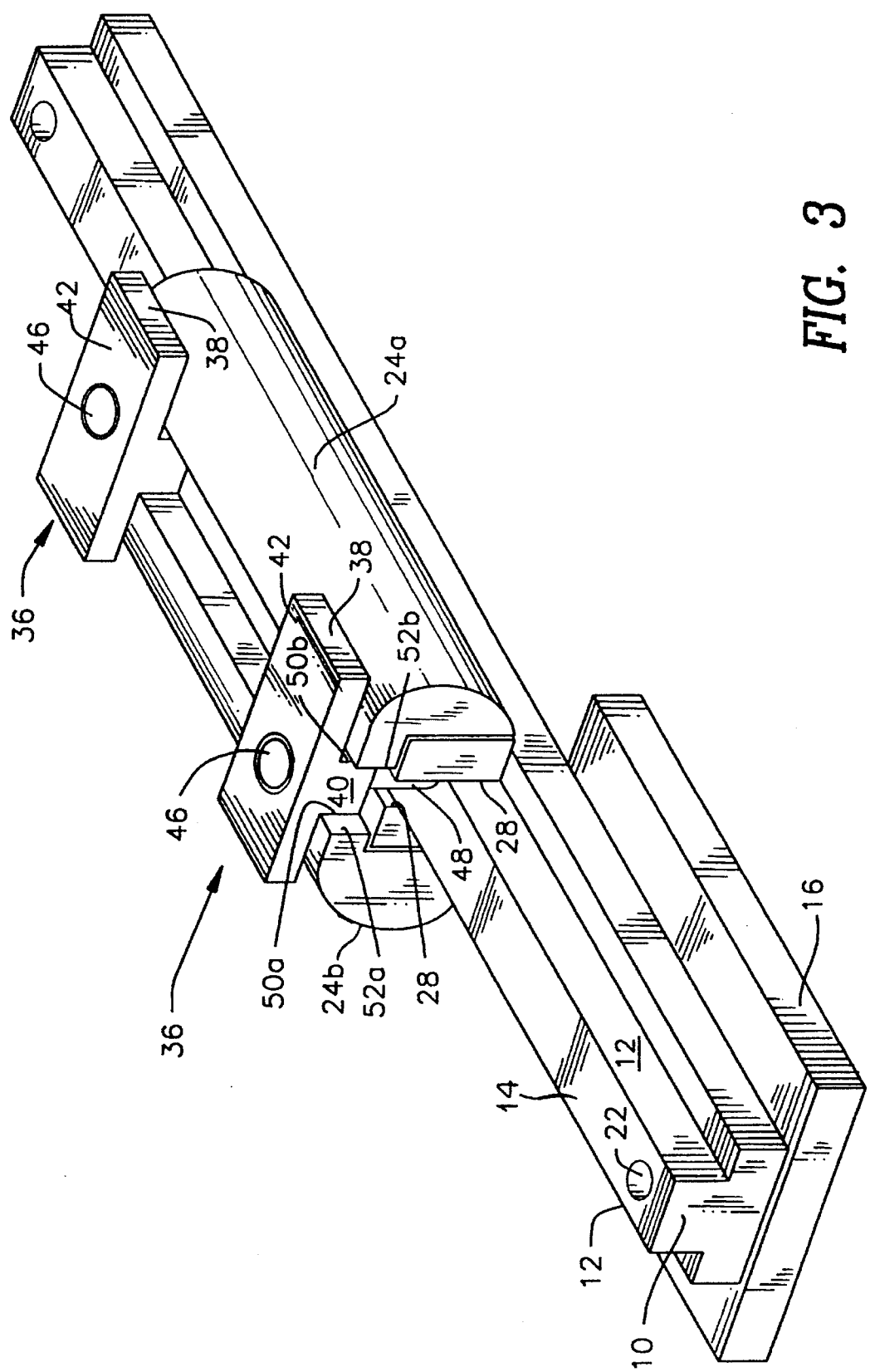
FIG. 3 is a bottom perspective view of the work station operatively secured to the jaws of a vise through the locking device.

The work station is secured in a vise 22 in a conventional manner through engagement with the opposed jaws 24a and 24b (shown best in FIG. 3). Each of the jaws has a bottom surface 6 and a side surface 28. The side surfaces 28 of the jaws 24a and 24b engage the respective side surfaces 12 of the projection 10. A force is applied to the jaws 24a and 24b by turning the handle 30 which moves a supporting member 32 so that the jaws 24 engage the projection 10.

Figure 2:
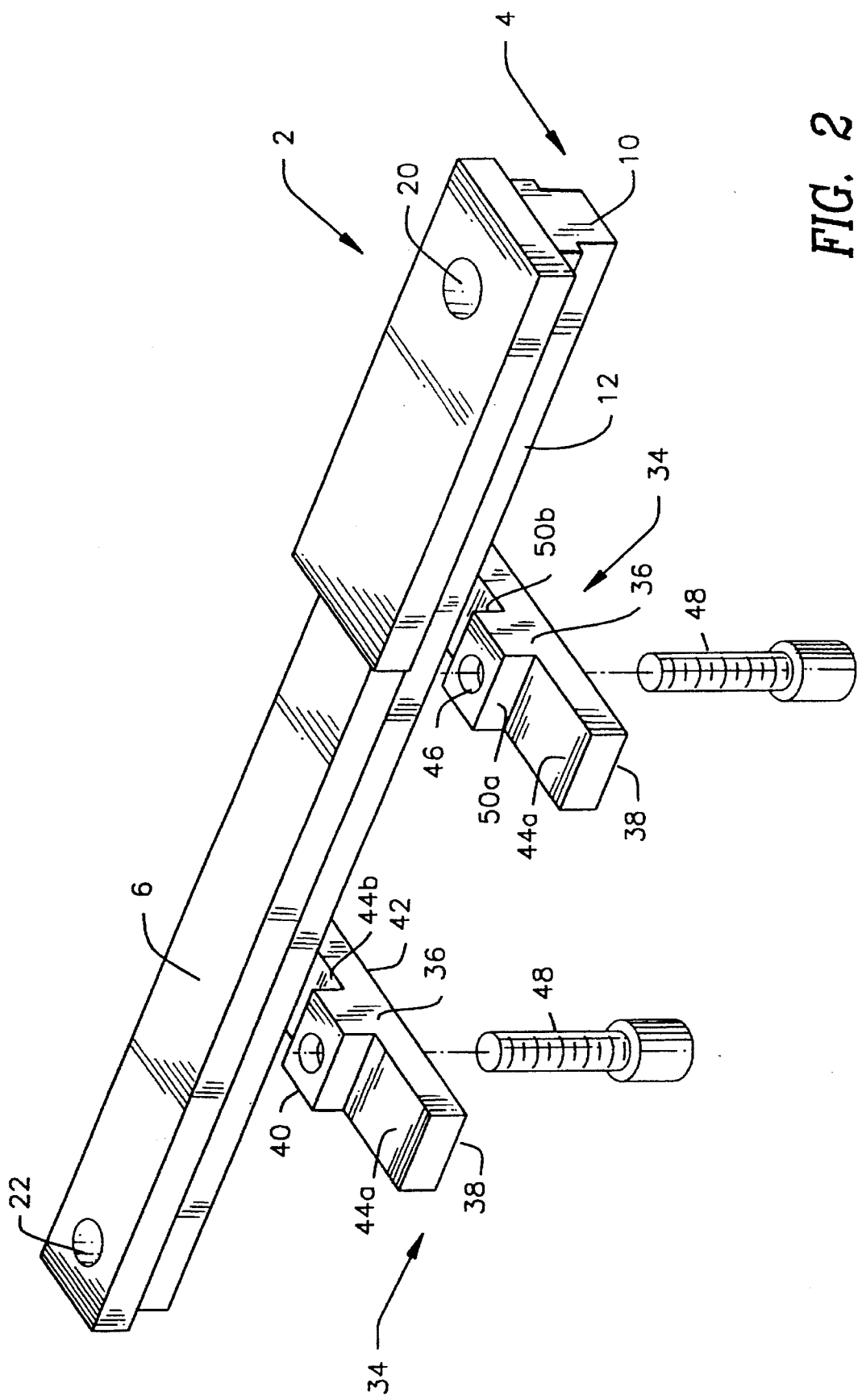
FIG. 2 is a perspective view of a portion of the locking device and its relationship to the work station.

In accordance with the present invention, the work station is secured to the vise through a unique locking assembly which engages the jaws of the vise as well as the work station to thereby lock the work station within the vise so that it cannot be moved. Referring to FIG. 2, the locking assembly 34 includes a T-shaped bar 36 having a base 38 and an upwardly extending projection 40. The base 38 has a bottom surface 42 and a pair of upper surfaces 44a and 44b separated by the projection 40. A hole 46 runs through the base 38 and projection 40 for housing a screw 48 or other securing device as explained hereinafter.

The projection 40 has opposed side surfaces 50a and 50b which are adapted to engage surfaces 52a and 52b of the jaws 24a and 24b to provide a further locking force to the work station 2 as it is secured to the vise 22.

The locking of the work station 2 within the vise 22 will now be explained. Referring to FIG. 3, the work station 2 is operatively engaged to the vise 22 by moving the jaws 24a and 24b until the side surfaces 28 thereof engage the side surfaces 12 of the projection 10. The lock device 34 is then applied to secure the work station to the vise.

The upper surfaces 44 of the projection 40 are placed into contact with the bottom surfaces 26 of the respective jaws 24a and 24b. The projection 40 therefore lies between the side surfaces 28 of the jaws 24a and 24b. When the jaws are tightened the surfaces 52a and 52b engage the side surfaces 50a and 50b of the projection 40 to provide an additional locking force in the same direction as the locking force applied by the jaws 24 against the work station 2.

In accordance with the present invention, a third locking force is applied to the work station in a direction perpendicular to the direction of the two locking forces previously described. More specifically and again referring to FIGS. 2 and 3, respective screws 48 are driven through the holes 46 of the T-shaped bar 36 and into respective holes 52 in the projection 10 of the elongated bar 4. As the screws 48 are tightened, the upper surfaces 44 of the base 38 exert a locking force against the respective bottom surfaces 26 of the jaws 24a and 24b. The resulting third locking force draws the jaws 24 and the work station into locking engagement.

Unlike conventional vises in which the jaws provide a single unidirectional line of force for locking, the present invention provides three locking forces, one of which is perpendicular to the other two. As a result, no matter where a force is applied to the work station, there is a significant resistance against the direction of force which enables the work station to remain locked in place within the vise.

What is claimed is:

1. Apparatus for use in conjunction with a vise having opposed jaws comprising:
    a) a work station having an upper side and a lower side, said upper side including a work surface and lower side comprising a vise engaging means;
    b) a vise engaging means operatively connected to the work station and having opposed sides for engagement by the opposed jaws of the vise to provide a first locking force to the work station in a first direction when the jaws of the vise engage the vise engaging means; and
    c) a locking assembly for securing the vise engaging means and the vise in operative locking engagement, said locking assembly comprising a T-shaped bar having respective surfaces for engaging the opposed jaws of the vise and securing means for securing the T-shaped bar to the vise engaging means, said locking assembly applying a second locking force to the work station in a second direction different than the first direction when the locking assembly is operatively secured to the vise engaging means of the work station.

2. The apparatus of claim 1 wherein the second direction is perpendicular to the first direction.

3. The apparatus of claim 1 wherein the vise engaging means comprises an elongated projection extending from the lower side of the vise engaging means, said projection having opposed sides for engaging the opposed jaws of the vise.

4. The apparatus of claim 1 wherein the T-shaped bar comprises a base having a bottom surface and opposed upper surfaces separated by an upwardly extending projection, said projection having a top surface and opposed side surfaces, said opposed upper surfaces of the base operatively engaging the bottom surface of the jaws of the vise to provide said second locking force.

5. The apparatus of claim 3 wherein said side surfaces of the T-shaped bar engage the side surfaces of the opposed jaws of the vise to generate a third locking force in the same direction as the first locking force.

6. The apparatus of claim 3 wherein the securing means comprise a screw-receiving hole passing through the base and the projection of the T-shaped bar, a screw-receiving hole in the elongated projection of the vise engaging means, said securing means insertable into the respective screw-receiving holes.

* * * * *